United States Patent
Shaepertoens et al.

(10) Patent No.: US 10,239,996 B2
(45) Date of Patent: Mar. 26, 2019

(54) PROCESS FOR PREPARING POLYMERS

(71) Applicant: IMPERIAL INNOVATIONS LIMITED, London (GB)

(72) Inventors: Marc Shaepertoens, London (GB); Piers Robert James Gaffney, London (GB); Gyorgy Szekely, London (GB); Andrew Guy Livingston, London (GB)

(73) Assignee: IMPERIAL INNOVATIONS LIMITED, London (GB)

( * ) Notice: Subject to any disclaimer, the term of this patent is extended or adjusted under 35 U.S.C. 154(b) by 0 days.

(21) Appl. No.: 15/502,012

(22) PCT Filed: Aug. 6, 2015

(86) PCT No.: PCT/GB2015/052287
§ 371 (c)(1),
(2) Date: Jun. 27, 2017

(87) PCT Pub. No.: WO2016/020696
PCT Pub. Date: Feb. 11, 2016

(65) Prior Publication Data
US 2017/0313818 A1  Nov. 2, 2017

(30) Foreign Application Priority Data
Aug. 6, 2014 (GB) .................................. 1413954.7

(51) Int. Cl.
| A61K 47/60 | (2017.01) |
| B01D 61/00 | (2006.01) |
| C08G 65/30 | (2006.01) |
| C08G 65/46 | (2006.01) |
| C08G 65/329 | (2006.01) |

(52) U.S. Cl.
CPC .............. *C08G 65/30* (2013.01); *A61K 47/60* (2017.08); *B01D 61/00* (2013.01); *C08G 65/329* (2013.01); *C08G 65/46* (2013.01); *B01D 2315/16* (2013.01); *C08G 2650/30* (2013.01); *C08G 2650/38* (2013.01); *C08G 2650/50* (2013.01); *C08G 2650/64* (2013.01); *C08L 2203/02* (2013.01)

(58) Field of Classification Search
CPC .... A61K 47/60; B01D 61/00; B01D 2315/16; C08G 65/30; C08G 65/329; C08G 65/46; C08G 2650/30; C08G 2650/38; C08G 2650/50; C08G 2650/64; C08L 2203/02
See application file for complete search history.

(56) References Cited

U.S. PATENT DOCUMENTS

| 3,772,264 | A | 11/1973 | Hoffmann-La Roche |
| 5,354,945 | A | 10/1994 | Detering et al. |
| 6,585,802 | B2 | 7/2003 | Koros et al. |
| 6,755,900 | B2 | 6/2004 | Koros et al. |
| 8,664,357 | B2 | 3/2014 | Livingston et al. |
| 2005/0089952 | A1 | 4/2005 | Chavez et al. |
| 2011/0245460 | A1 | 10/2011 | Livingston et al. |
| 2012/0205250 | A1* | 8/2012 | Lee .......................... C25D 3/38 205/296 |
| 2013/0072691 | A1* | 3/2013 | Livingston ........... C08G 65/325 548/478 |

FOREIGN PATENT DOCUMENTS

| GB | 2369311 A | 5/2002 |
| WO | 94/29362 A1 | 12/1994 |
| WO | 2007125367 A1 | 11/2007 |
| WO | 2011148177 A2 | 12/2011 |

OTHER PUBLICATIONS

Osada et al., "Polymeric micelles from poly(ethylene glycol)-poly(aminoacid) block copolymer for drug and gene delivery," J. R. Soc . Interface (2009) 6, S325-S339. (Year: 2009).*
International Search Report for PCT/GB2015/052287 dated Oct. 23, 2015, p. 1-4.
J Kim et al., In Situ Solvent Recovery by Organic Solvent Nanofiltration, ACS Sustainable Chem. Eng. 2014, 2, 2371-2379.
L. Hartmannet al., Precision Polymers: Monodisperse,Monomer-Sequence-Defined Segments to Target Future Demands of Polymers in Medicine.Adv. Mater. 2009, 21, 3425-3431.
Lutz J.F. et al., Sequence-Controlled Polymers Science, vol. 341, No. 6146, 1238149, Sep. 9, 2013, p. 628, 1-8.
Marchetti et al., Molecular Separation with Organic Solvent Nanofiltration, Chem. Rev. 2014, 114, p. 10735?10806.
Vandezande et al., Solvent resistant nanofiltration: separating on a molecular level, Chem. Soc. Rev., 2008, 37, 365-405.

* cited by examiner

Primary Examiner — Pancham Bakshi
Assistant Examiner — Mark R Luderer
(74) Attorney, Agent, or Firm — McCarter & English, LLP; Steven G. Davis; Wei Song

(57) ABSTRACT

A process for preparing non-naturally-occurring defined monomer sequence polymers is provided, and in which a high degree of synthetic control is obtained by the use of solvent resistant diafiltration membranes. Also provided is a process for separating non-naturally-occurring defined monomer sequence polymers from synthetic by-products or excess reagents using solvent resistant diafiltration membranes, and a use of a solvent resistant diafiltration membrane in processes for preparing and separating non-naturally-occurring defined monomer sequence polymers.

15 Claims, 5 Drawing Sheets

PROCESS FOR PREPARING POLYMERS

RELATED APPLICATION INFORMATION

This application is a § 371 of International Application No. PCT/GB2015/052287, filed Aug. 6, 2015, which claims priority to GB Application No. 1413954.7, filed Aug. 6, 2014, the contents of each of which are herein incorporated by reference in their entirety.

INTRODUCTION

The present invention relates to a process for the preparation of non-naturally-occurring defined monomer sequence polymers. More particularly, the defined monomer sequence polymers formed by the process of the invention are defined as having at least two or more monomers that are structurally distinct from each other. The present invention also relates to the use of organic solvent resistant membranes in the polymer preparation processes of the invention.

BACKGROUND OF THE INVENTION

The primary structure of non-naturally-occurring polymeric materials—that is, the sequential arrangement of monomer units in a polymer chain—is generally poorly controlled in synthetic macromolecules. Common non-natural polymers are usually homopolymers, made of the same monomer unit, or copolymers with simple chain microstructures, such as random or block copolymers. These polymers are used in many areas but do not have the structural and functional complexity of defined sequence biopolymers, such as oligonucleotides, nucleic acids, proteins peptides, or oligosaccharides.

There is great utility in defined monomer sequence non-naturally-occurring polymers, i.e. non-biological polymers which are assembled from a library of functional building blocks so that the monomer order is exactly defined, and in which at least two or more of the monomers are structurally distinct from each other. For such molecules it may be possible to programme their structural properties, for example folding and self-assembly, and also their macroscopic properties (Lutz J-F et al., "Sequence-Controlled Polymers", Science 9 Aug. 2013, Vol 341, page 628.) Many applications in medicine are also envisaged (Hartmann L and Borner H G, "Precision Polymers: Monodisperse, Monomer-Sequence-Defined Segments to Target Future Demands of Polymers in Medicine" Advanced Materials. 2009, Vol 21, pp 3425-3431).

A key challenge for defined monomer sequence polymers formed from non-naturally-occurring monomers is how to prepare them. Various strategies have been proposed, including biological methods and chemical synthesis using iterative steps in which the monomers are attached one-by-one in a given order. This method suffers from the difficulties of purification at each step. This challenge has been addressed to date (Lutz J-F et al., "Sequence-Controlled Polymers", Science 9 Aug. 2013, Vol 341, page 628. and Hartmann L and Borner H G, "Precision Polymers: Monodisperse, Monomer-Sequence-Defined Segments to Target Future Demands of Polymers in Medicine" Advanced Materials. 2009, Vol 21, pp 3425-3431) through either advanced polymerisation chemistry or solid phase synthesis as used for sequence defined biopolymers, such as oligonucleotides and peptides.

Membrane processes are well known in the art of separation science, and can be applied to a range of separations of species of varying molecular weights in liquid and gas phases (see for example "Membrane Technology" in Kirk Othmer Encyclopaedia of Chemical Technology, 4$^{th}$ Edition 1993, Vol 16, pages 135-193). Nanofiltration is a membrane process utilising membranes whose pores are in the range 0.5-5 nm, and which have molecular weight (MW) cut-offs in the range of 200-3,000 Daltons. Nanofiltration has been widely applied to filtration of aqueous fluids, but due to a lack of suitable solvent stable membranes has not been widely applied to separation of solutes in organic solvents. Ultrafiltration membranes typically have MW cut-offs in the range 3,000 to 1,000,000 Daltons. Recently new classes of membranes have been developed which are stable in even the most difficult solvents as reported in P. Vandezande, L. E. M. Gevers and I. F. J. Vankelecom *Chem. Soc. Rev.*, (2008), Vol 37, pages 365-405, some of which may be suitable for Organic Solvent Nanofiltration (OSN). Such membranes may be polymeric membranes, ceramic membranes, or mixed inorganic/organic membranes.

Membrane processes have been combined with chemical synthesis for the production of sequence defined biopolymers such as peptides and oligonucelotides. The use of membranes during peptide synthesis to separate growing peptides from excess reagents and reaction by-products was reported in U.S. Pat. No. 3,772,264. Peptides were synthesised in a liquid phase, with poly(ethylene glycol) (PEG) as a molecular anchoring group, and separation of the growing peptide chain from impurities was achieved with aqueous phase ultrafiltration. The separation required evaporation of the organic solvent after each coupling step, neutralisation followed by evaporation after each deprotection, and then for either coupling or deprotection, water uptake before ultrafiltration from an aqueous solution. Water was then removed by evaporation and/or azeotropic distillation before re-dissolving the PEG anchored peptide back into organic solvent for the next coupling or deprotection step.

U.S. Pat. No. 8,664,357 reports the use of organic solvent nanofiltration membranes in a process for preparing biopolymers selected from oligonucleotides, peptides and peptide nucleic acids.

US Patent Application US 20130072691 A1 describes the use of organic solvent nanofiltration membranes in the preparation of monodisperse (i.e. of similar or equal molecular weight), heterobifunctional (having a different functional group at either end of the polymer) synthetic polymers based on polyethylene glycol.

Research to date has focused on the provision of biopolymers (such as oligonucleotides, peptides and peptide nucleic acids) having a defined sequence of monomeric units. Given their widespread applicability, there remains a need for a process for preparing non-naturally-occurring defined monomer sequence polymers.

The present invention was devised with the foregoing in mind.

SUMMARY OF THE INVENTION

According to a first aspect of the present invention there is provided a process for the preparation of a first compound being a non-naturally-occurring defined monomer sequence polymer, in which at least two of the monomer units are distinct from each other; the process comprising the steps of:
  (i) synthesising the first compound by performing one or more sequential monomeric coupling reactions in a first organic solvent, and
  (ii) between each coupling reaction, separating a product of said one or more sequential coupling reactions from at least one second compound, which is a reaction by-product of the synthesis of the product and/or an excess of a reagent used for the synthesis of the product;

wherein during step (ii) the product of said one or more sequential coupling reactions and at least one second compound are dissolved in a second organic solvent and are separated by a process of diafiltration using a membrane that is stable in the organic solvent and which provides a rejection for the product which is greater than the rejection for the second compound.

According to a second aspect of the present invention, there is provided a process for the preparation of a first compound being a defined monomer sequence polymer in which at least two of the monomer units are distinct from each other; the process comprising the steps of:

(i) synthesising the first compound by performing one or more sequential monomeric coupling reactions in a first organic solvent, and (ii) between each coupling reaction, separating a product of said one or more sequential coupling reactions from at least one second compound, which is a reaction by-product of the synthesis of the product and/or an excess of a reagent used for the synthesis of the product;

wherein during step (ii) the product of said one or more sequential coupling reactions and at least one second compound are dissolved in a second organic solvent and are separated by a process of diafiltration using a membrane that is stable in the organic solvent and which provides a rejection for the product which is greater than the rejection for the second compound, with the proviso that the first compound is not an oligonucleotide, peptide or peptide nucleic acid.

According to a third aspect of the present invention there is provided a process for the separation of a first compound from a second compound in an organic solvent feed stream, the process comprising the step of contacting the feed stream with a diafiltration membrane that is stable in the organic solvent and which provides a rejection for the first compound which is greater than the rejection for the second compound, wherein (i) the first compound is a non-naturally-occurring defined monomer sequence polymer, in which at least two of the monomer units are distinct from each other; and (ii) the second compound is a by-product of a reaction forming the first compound and/or a reagent used in said reaction.

According to a fourth aspect of the present invention there is provided a process for the separation of a first compound from a second compound in an organic solvent feed stream, the process comprising the step of contacting the feed stream with a diafiltration membrane that is stable in the organic solvent and which provides a rejection for the first compound which is greater than the rejection for the second compound, wherein (i) the first compound is a defined monomer sequence polymer in which at least two of the monomer units are distinct from each other; and (ii) the second compound is a by-product of a reaction forming the first compound and/or a reagent used in said reaction, with the proviso that the first compound is not an oligonucleotide, peptide or peptide nucleic acid.

According to a fifth aspect of the present invention, there is provided a use of an organic solvent resistant diafiltration membrane in a process defined herein.

According to a sixth aspect of the present invention, there is provided a defined monomer sequence polymer obtainable, obtained or directly obtained by a process defined herein.

DETAILED DESCRIPTION OF THE INVENTION

Definitions

The term "monomer" or "monomeric unit" is used herein to refer to a polymer building block which has a defined and unique molecular structure and which can be reacted to form a part of a polymer.

The term "defined monomer sequence polymer" is used herein to refer to a polymer comprising at least two monomers in which at least two of the monomers are distinct from each other and in which the monomers are present in the same order in the polymer chain for all molecules of the polymer.

The terms "non-natural" and "non-naturally-occurring" are synonymously used herein to denote manmade entities that do not exist in nature. By way of example, it will be understood that such terms cannot be applied to entities that are wholly natural (e.g. oligonucleotides and peptides). It will also be understood that such terms cannot be applied to entities, in which the polymeric backbone is wholly formed from amino acids and/or sugar phosphates (e.g. in the case of oligonucleotides, peptides and peptide nucleic acids). For the avoidance of doubt, it will be understood that the terms "non-natural" and "non-naturally-occurring" can be applied to polymers in which the polymeric backbone is wholly formed from amino acids and/or sugar phosphates, save for a single monomer having a non-naturally-occurring backbone moiety (e.g. a poly(ethylene glycol) backbone moiety). Similarly, it will be understood that the terms "non-natural" and "non-naturally-occurring" can be applied to polymers in which the polymeric backbone is wholly formed from non-naturally-occurring backbone moieties (e.g. poly(ethylene glycol) backbone moieties).

The term "synthesis support" is used herein to relate to a chemical entity that allows the first compound to stay in solution during the reaction and diafiltration step, and optionally to provide an increased molecular bulk to enhance membrane separation. The synthesis support may be a branch point molecule, or a polymer, dendrimer, dendron, hyperbranched polymer, or organic/inorganic materials, including nanoparticles, fullerenes and 2-D materials such as graphene and boron nitride.

The term "branch point molecule" is used herein to refer to a polyfunctional organic molecular "hub", having at least 2 reactive moieties, and the ability to covalently bind to a terminal of an initial monomer.

Processes of the Invention

As discussed hereinbefore, the present invention provides a process for the preparation of a first compound being a non-naturally-occurring defined monomer sequence polymer, in which at least two of the monomer units are distinct from each other; the process comprising the steps of:

(i) synthesising the first compound by performing one or more sequential monomeric coupling reactions in a first organic solvent, and (ii) between each coupling reaction, separating a product of said one or more sequential coupling reactions from at least one second compound, which is a reaction by-product of the synthesis of the product and/or an excess of a reagent used for the synthesis of the product;

wherein during step (ii) the product of said one or more sequential coupling reactions and at least one second compound are dissolved in a second organic solvent and are separated by a process of diafiltration using a membrane that is stable in the organic solvent and which provides a rejection for the product which is greater than the rejection for the second compound.

The defined monomer sequence polymers are non-naturally-occurring due to the fact that at least one of the monomeric units comprised by the polymer has a backbone moiety that is non-naturally-occurring (i.e. the monomer does not comprise a peptide or sugar phosphate moiety that forms part of the polymer backbone). In an embodiment, more than one of the monomeric units comprised by the polymer has a backbone moiety that is non-naturally-occurring. In another embodiment, the polymeric backbone of the entire polymer is formed from non-naturally-occurring moieties (i.e. it does not comprise any peptide or sugar phosphate moieties).

In one embodiment, more than 10% of the monomeric units comprised by the polymer have a backbone moiety that is non-naturally-occurring. In another embodiment, more than 30% of the monomeric units comprised by the polymer have a backbone moiety that is non-naturally-occurring. In another embodiment, more than 50% of the monomeric units comprised by the polymer have a backbone moiety that is non-naturally-occurring. In another embodiment, more than 70% of the monomeric units comprised by the polymer have a backbone moiety that is non-naturally-occurring. In another embodiment, more than 90% of the monomeric units comprised by the polymer have a backbone moiety that is non-naturally-occurring.

It will be understood that step (i) refers to one or more sequential monomeric (as opposed to polymeric) coupling reactions. It will be clear to the person skilled in the art that the term "monomeric" pertains to a minimum repeating unit.

Having regard to step (i) discussed above, it will be understood that the "first compound" may be a defined monomer sequence polymer containing only two monomer units, in which case the polymer is synthesised by the coupling of an initial monomer unit with a first additional monomer unit. It will also be understood that the "first compound" may be a defined monomer sequence polymer containing three monomer units, in which case the polymer is synthesised by first coupling an initial monomer unit with a first additional monomer unit, then coupling the first additional monomer unit with a second additional monomer unit. Accordingly, "first compounds" containing 4, 5 and 6 monomer units are respectively synthesised by sequential coupling of the third, fourth and fifth additional monomer units to the second, third and fourth additional monomer units respectively.

Still having regard to step (i), any suitable method of synthesising the first compound that is known in the art may be utilised. In an embodiment, the synthesis of the first compound may involve one or more coupling and deprotection reactions. In such cases, step (i) comprises reacting an initial monomer unit with an excess of a first additional monomer unit in which one of the reactive terminals has been protected using a protecting group. Once the initial monomer and the first additional monomer have been coupled, the protecting group is cleaved to expose the reactive terminal of the first additional monomer, which is then ready for coupling with a second additional monomer.

Hence, in an embodiment, the one or more monomeric coupling reactions of step (i) each comprise the steps of:

a. reacting a starting material with an excess of an additional monomer, the additional monomer having one or its reactive terminal protected by a protecting group, and b. removing the protecting group so as to expose the reactive terminal such that it is ready for reaction with a subsequent additional monomer, wherein the starting material is either an initial monomer having at least one of its reactive terminals protected, or the polymeric product of the one or more sequential monomeric coupling reactions. In such embodiments, step (ii) may be performed after step a) (in order to remove excess unreacted additional monomers and optionally other small reaction debris) and step b) (in order to remove the cleaved protecting group, by products of the protecting group removal and one or more deprotection reagents). It will be understood that the term "reagent" appearing in step (ii) encompasses both reactants and catalysts.

In one embodiment, during synthesis of the first compound, the product of the one or more sequential monomeric coupling reactions is covalently attached to a synthesis support by an initial monomer unit. The initial monomer unit may be directly attached to the synthesis support, or indirectly attached thereto via a linker moiety (such as a dicarboxylic acid moiety). The synthesis support may be a branch point molecule, or a polymer, dendrimer, dendron, hyperbranched polymer, or organic/inorganic nanoparticle. Once the desired defined monomer sequence polymer has been synthesised, the synthesis support is cleaved from the initial monomer and separated therefrom to reveal the first compound.

When used as a synthesis support, suitable polymers include polycondensation matrices or polymerisation matrices containing heteroatom functions. Such heteroatom functions may contain oxygen, nitrogen, or can contain more than one heteroatom, such as acid amide groups. Examples of polymeric synthesis supports include polyalkylene glycols including polyethylene glycol, polycaprolactone, polyethylene glycol esterified with citric acid, copolymers of polyethyleneglycol and succinic acid, of vinylpyrrolidone and acrylic acid or b-hydroxy-ethylacrylate; or of acrylamide and vinylactetate.

When used as a synthesis support, suitable dendrimers include poly(amidoamine), also known as PAMAM dendrimers; phosphorous dendrimers; polylysine dendrimers; and polypropylenimine (PPI) dendrimers which can have surface functionalities including —OH, —$NH_2$, -PEG, and COOH groups.

When used as a synthesis support, suitable nanoparticles may be prepared from $SiO_2$, $TiO_2$, or other organic or inorganic materials including fullerenes or 2-D materials such as graphene.

In another embodiment, the synthesis support is a branch point molecule (i.e. a polyfunctional molecule) having two or more reactive moieties capable of covalently binding to the initial monomer unit. Chemistries suitable for covalently binding the initial monomer unit to the branch point molecule will be readily apparent to a person of skill in the art, and include amide, ester, ether and silyl ether couplings.

In another embodiment, the branch point molecule may have any of the structures shown below:

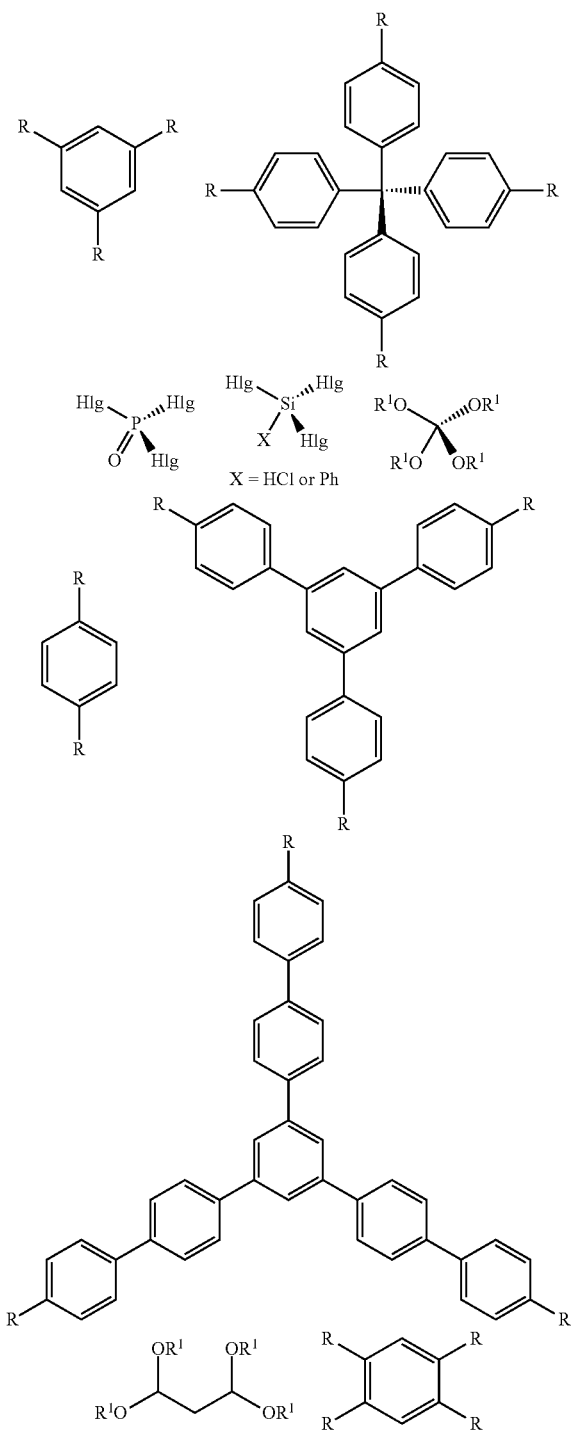

Hlg = Halogen
R = COOH, COHlg, CH₂Hlg
R¹ = alkyl

In an embodiment, the initial monomer is reacted in excess with a synthesis support, allowing for the synthesis of a conjugate that can be purified from the excess initial monomer. Subsequently, the first compound may be obtained through a succession of coupling/deprotection reactions using one or more additional monomers.

The cleavage of the polymer chains from the branch point molecule is undertaken to yield substantially the final defined monomer sequence polymer with any modifications made to the free unbound terminal end of the initial monomer. The choice of the cleavage reaction used to detach the polymer from the branch point molecule is dependent on the product one desires to synthesise and can be performed at the end of the synthetic strategy or at any stage, according to convenience.

In another embodiment, the monomer units collectively forming the first compound each have a backbone moiety and at least one of the monomer units has a pendent side chain moiety. In a further embodiment, all of the monomeric units have side chain moieties.

In an embodiment, at least three of the monomer units are distinct from each other. Suitably, at least four of the monomer units are distinct from each other. More suitably, at least five of the monomer units are distinct from each other. In a particular embodiment, all of the monomeric units constituting the defined monomer sequence polymer are distinct from each other.

In a particular embodiment, all of the monomeric units coupled during step (i) (and hence forming the first compound) have an identical backbone moiety, but at least two of the monomer units are distinct from each other by virtue of their respective side chain moieties. It will be understood that where only one of the monomeric units has a pendent side chain moiety, two of the monomer units forming the polymer are nonetheless distinct from each other by virtue of their respective side chain moieties, in the sense that one of the monomers has a side chain moiety and the other does not. In such embodiments, the first compound may have a backbone selected from poly(ethylene glycol) (PEG), poly(propylene glycol) (PPG), poly(butylene glycol), poly(ethylene oxide), poly(propylene oxide), poly(butylene oxide), poly(dimethylsiloxane) (PDMS), polybutadiene, polysioprene, polystyrene, nylons and polyesters, poly(ethylene imines) (PEI), poly(propylene imines), poly(L-Lysine) (PLL), poly(amidoamines) (PAA), poly(methyl methacrylate) (PMMA), poly(vinyl benzoic acid), poly(hydroxystyrene), N-substituted glycines, and poly(lactide-co-glycolide) (PLGA).

In an alternative embodiment, not all of the monomeric units coupled during step (i) (and hence forming the first compound) have identical backbone moieties. In such embodiments, the first compound may be a copolymer having a backbone selected from two or more of poly(ethylene glycol) (PEG), poly(propylene glycol) (PPG), poly(butylene glycol), poly(ethylene oxide), poly(propylene oxide), poly(butylene oxide), poly(dimethylsiloxane) (PDMS), polybutadiene, polysioprene, polystyrene, nylons and polyesters, poly(ethylene imines) (PEI), poly(propylene imines), poly (L-Lysine) (PLL), poly(amidoamines) (PAA), poly (methyl methacrylate) (PMMA). Poly (vinyl benzoic acid), poly(hydroxystyrene), N-substituted glycines, and poly(lactide-co-glycolide) (PLGA). In such embodiments, the side chain groups of the monomer units may be identical or different.

In an alternative embodiment, at least two of the monomeric units coupled during step (i) (and hence forming the first compound) are distinct from each other by virtue of both their respective side chain moieties and their backbones.

In a particular embodiment, all of the monomer units coupled during step (i) (and hence forming the first compound) have an identical backbone moiety, but at least two of the monomer units are distinct from each other by virtue of their respective side chain moieties. Suitably, all of the monomer units have an alkylene glycol (e.g. ethylene glycol) backbone moiety, resulting in a poly(alkylene glycol) (e.g. poly(ethylene glycol)) polymeric backbone.

In another particular embodiment, at least one of the monomeric units coupled during step (i) has chirality.

In another particular embodiment, at least two of the monomer units sequentially coupled in step (i) are distinct from each other by virtue of their stereochemistry. In such embodiments, the monomeric units may be identical in structure, but different in terms of the spatial arrangement of the atoms present.

In another particular embodiment, at least one of the monomeric units coupled during step (i) comprises a side chain bound to a chiral carbon atom present within the backbone moiety. Suitably, at least two of the monomeric units comprise side chains, each being bound to a chiral carbon atom present within the backbone moiety. The side chains may be the same or different in terms of their structure and stereochemistry.

In another particular embodiment, all of the monomer units sequentially coupled in step (i) (and hence forming the first compound) have an identical alkylene glycol backbone moiety (e.g. an ethylene glycol backbone moiety), but at least two of the monomer units are distinct from each other by virtue of their respective side chain moieties, each of said side chain moieties being bound to a chiral carbon atom present within the backbone moiety, and wherein the side chain moieties are distinct from one another in terms of their structure or their stereochemistry or both.

Where present, the side chain moieties or moiety of the monomeric units sequentially coupled in step (i) (and hence forming the first compound) may take the form of an active ingredient (for example, an active pharmaceutical ingredient), or an active ingredient tethered to the backbone moiety via a suitable linking group. The linking group may be such that the defined monomer sequence polymer can release the active ingredient in response to change in environment (for example pH, the expression of certain enzymes or one or more conditions being specific to a disease site microenvironment). In such embodiments, the present invention permits the preparation of defined monomer sequence polymers having a molecular weight suitable for achieving effective delivery of an active ingredient within an organism. For example, the present invention permits the preparation of defined monomer sequence polymers having a molecular weight greater than the glomerular filtration threshold required for renal clearance, meaning that the defined monomer sequence polymer is circulated in the organism for a prolonged period of time. Alternatively, the defined monomer sequence polymers may be prepared to have a molecular weight that is lower than the glomerular filtration threshold required for renal clearance, meaning that the polymer is readily cleared from the body after having released its payload. In such embodiments, it will be understood that the monomeric units coupled during step (i) which have side chain moieties comprising active ingredients must be small enough (e.g. in terms of molecular weight) to pass through the membrane during step (ii) of the process, otherwise it would be impossible to separate the growing polymer from excess monomeric units.

In an embodiment, the side chain moieties or moiety may take the form of a plurality of different active ingredients (for example, active pharmaceutical ingredients), or linking groups tethered to different active ingredients. The different active ingredients may be coupled to the defined monomer sequence polymer in a predetermined ratio, thereby facilitating the administration of combination therapies.

In another embodiment, the side chain moieties or moiety may take the form of a targeting group (e.g. a specific ligand or antibody) that serves to help direct the defined monomer sequence polymer to a relevant site within an organism for subsequent release of an active payload.

In another embodiment, the first solvent (i.e. that used in step (i)) and the second solvent (i.e. that used in step (ii)) may be the same or different. Suitably, the solvent used for the diafiltration should maintain the polymer and/or the functionalised polymer in solution. Exemplary solvents include aromatics, alkanes, ketones, glycols, chlorinated solvents, esters, ethers, amines, nitriles, aldehydes, phenols, amides, carboxylic acids, alcohols, furans, and dipolar aprotic solvents, and mixtures thereof and with water. Specific examples of solvents include toluene, xylene, benzene, styrene, anisole, chlorobenzene, dichlorobenzene, chloroform, dichloromethane, dichloroethane, methyl acetate, ethyl acetate, butyl acetate, methyl ether ketone (MEK), methyl iso butyl ketone (MIBK), acetone, ethylene glycols, ethanol, methanol, propanol, butanol, hexane, cyclohexane, dimethoxyethane, methyl tert butyl ether (MTBE), diethyl ether, adiponitrile, N,N dimethylformamide, dimethylsulfoxide, N,N dimethylacetamide, dioxane, nitromethane, nitrobenzene, pyridine, carbon disulfide, tetrahydrofuran, methyl-tetrahydrofuran, N-methyl pyrrolidone, N-ethyl pyrrolidone, acetonitrile, and mixtures thereof and with water.

Suitable membranes for use in the invention include polymeric and ceramic membranes, and mixed polymeric/inorganic membranes. Membrane rejection $R_i$ is a common term known by those skilled in the art and is defined as:

$$R_i = \left(1 - \frac{C_{P,i}}{C_{R,i}}\right) \times 100\% \qquad \text{eq. (1)}$$

where $C_{P,i}$=concentration of species i in the permeate, permeate being the liquid which has passed through the membrane, and $C_{R,i}$=concentration of species i in the retentate, retentate being the liquid which has not passed through the membrane. It will be appreciated that a membrane is suitable for the invention if $R_{\text{(defined monomer sequence polymer OR conjugate)}} > R_{\text{(at least one reaction by-product or reagent)}}$.

The membrane of the present invention may be formed from any polymeric or ceramic material which provides a separating layer capable of preferentially separating the first molecule or conjugate from at least one reaction by-product or reagent. Preferably the membrane is formed from or comprises a material selected from polymeric materials suitable for fabricating microfiltration, ultrafiltration, nanofiltration or reverse osmosis membranes, including polyethylene, polypropylene, polytetrafluoroethylene (PTFE), polyvinylidene difluoride (PVDF), polysulfone, polyethersulfone, polyacrylonitrile, polyamide, polyester, polyimide, polyetherimide, cellulose acetate, polyaniline, polypyrrole, polybenzimidazole, polyetheretherketone (PEEK) and mixtures thereof. The membranes can be made by any technique known in the art, including sintering, stretching, track etching, template leaching, interfacial polymerisation or phase inversion. More preferably, membranes may be crosslinked or treated so as to improve their stability in the reaction solvents. PCT/GB2007/050218 describes membranes which may be suitable for use in the present invention.

In a particular embodiment, the membrane is a composite material and the non-porous, selectively permeable layer thereof is formed from or comprises a material selected from modified polysiloxane based elastomers including polydimethylsiloxane (PDMS) based elastomers, ethylene-propylene diene (EPDM) based elastomers, polynorbornene based elastomers, polyoctenamer based elastomers, polyurethane based elastomers, butadiene and nitrile butadiene rubber based elastomers, natural rubber, butyl rubber based elastomers, polychloroprene (Neoprene) based elastomers, epichlorohydrin elastomers, polyacrylate elastomers, polyethylene, polypropylene, polytetrafluoroethylene (PTFE), polyvinylidene difluoride (PVDF) based elastomers, polyetherblock amides (PEBAX), polyurethane elastomers, crosslinked polyether, polyamides formed by interfacial polymerisation, and mixtures thereof.

In another embodiment, the membrane is prepared from an inorganic material (e.g. silicon carbide, silicon oxide, zirconium oxide, titanium oxide, or zeolites), using any technique known to those skilled in the art such as sintering, leaching or sol-gel processes.

In another embodiment, the membrane comprises a polymer membrane with dispersed organic or inorganic matrices in the form of powdered solids present at amounts up to 20 wt % of the polymer membrane. Carbon molecular sieve matrices can be prepared by pyrolysis of any suitable material as described in U.S. Pat. No. 6,585,802. Zeolites as described in U.S. Pat. No. 6,755,900 may also be used as an inorganic matrix. Metal oxides, such as titanium dioxide, zinc oxide and silicon dioxide may be used, for example the materials available from Evonik Industries (Germany) under their Aerosol and AdNano trademarks. Mixed metal oxides such as mixtures of cerium, zirconium, and magnesium oxides may be used. Graphene, graphene oxide, metal organic frameworks (MOFs), boron nitride, carbon nanotubes may be used. Preferred matrices will be particles less than 1.0 micron in diameter, preferably less than 0.1 microns in diameter, and preferably less than 0.01 microns in diameter.

As discussed hereinbefore, the present invention also provides a process for the separation of a first compound from a second compound in an organic solvent feed stream, the process comprising the step of contacting the feed stream with a diafiltration membrane that is stable in the organic solvent and which provides a rejection for the first compound which is greater than the rejection for the second compound, wherein
(i) the first compound is a non-naturally-occurring defined monomer sequence polymer, in which at least two of the monomer units are distinct from each other; and
(ii) the second compound is a by-product of a reaction forming the first compound and/or a reagent used in said reaction.

It will be understood that features common to both the first and second, and third and fourth, aspects of this invention may be further defined by reference to any of the definitions, embodiments and examples recited in the preceding paragraphs.

Uses of the Invention

As discussed hereinbefore, the present invention also provides a use of an organic solvent resistant diafiltration membrane in a process defined herein.

It will be understood that features common to both the processes and uses of this invention may be further defined by reference to any of the definitions, embodiments and examples recited in the preceding paragraphs.

EXAMPLES

The invention will now be exemplified, for the purpose of reference and illustration only, with reference to the accompanying figures, in which.

Example 1

Figure 1:
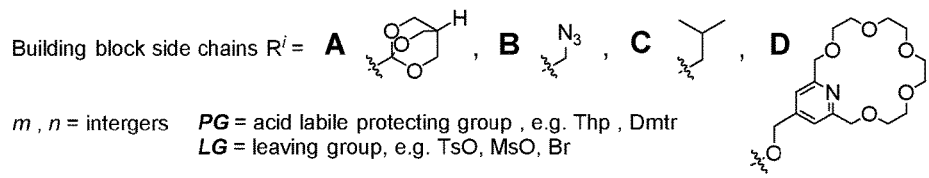
FIG. 1 illustrates a synthesis strategy to prepare various defined monomer sequence polymers based on a PEG backbone.
Figure 1:
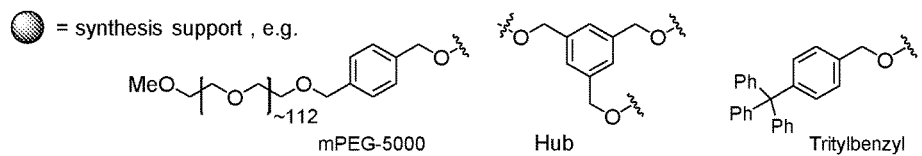
Figure 1:
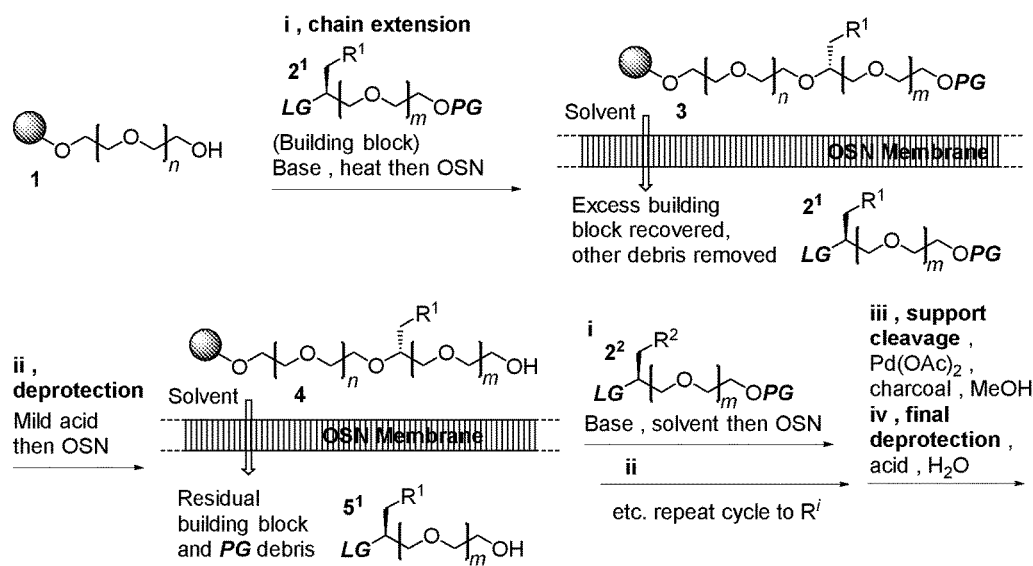

Preparation of a Sequence Defined Polymer Based on a PEG Backbone:

A synthesis support is selected with a benzylic reactive site that may be cleaved by hydrogenolysis at the end of the synthesis (FIG. 1). For instance a long chain, monomethoxy-PEG (mPEG-5000) may be treated with vinylchloromethylbenzene, and the vinyl unit of the resultant mPEG-styrene transformed to a bromomethyl group; commercially available 1,3,5-tribromomethyl benzene may be used directly as a three-armed hub; functional group interconversion of readily prepared mono-amino tetraphenylmethane provides ready access to a bulky 4-tritylbenzyl support.

A length of PEG backbone is first prepared, using oligoethylene glycol building blocks lacking any side chains, using the manipulations reported in G. Szekely, M. Schaepertoens, P. R. J. Gaffney, A. G. Livingston *Polymer Chem.*, (2014), Vol 5, pages 694-697; *Chem. Eur. J*, (2014), DOI: 10.1002/chem.201402186. The initial region of monodisperse PEG may then be extended with non-identical building blocks to prepare a defined monomer sequence polymer. These new building blocks (2), bearing side-chains with added functionality, are prepared by chemical synthesis: For instance, the 3-C hydroxymethyl group of glycerol acetonide may be transformed into $R^1$, followed by unblocking of the acetonide and conversion of the resultant diol into a short PEG chain; olefins such as 5-methyl 1-hexene (side-chain C) are also readily transformed by asymmetric dihyrdoxylation into a diol precursor of building block 2, and a similar approach with initial protection/functional group manipulation may be used to prepare other building blocks from 3-butenoic acid (A) or 3-butenol (B and D). Building blocks 2 are similar to those already reported to prepare monodisperse PEGs (see G. Szekely, M. Schaepertoens, P. R. J. Gaffney, A. G. Livingston), consisting of a short oligo ethylene glycol backbone of exactly defined length, having at one end a temporary, mild acid labile protecting group (PG), and at the other a leaving group (LG) susceptible to displacement by an alkoxide nucleophile during chain extension by Williamson etherification. The side chains (e.g. A to D, FIG. 1) are either inert to such conditions, or bear reactive functional groups masked by permanent protecting groups that are removed at the end of the synthesis.

Supported monodisperse PEG 1 is treated with an excess of the first non-identical building block ($2^1$) under strongly basic conditions to extend the sequence defined polymer backbone. The crude reaction mixture containing the desired sequence defined polymer (3) bearing the first side-chain ($R^1$) is purified by diafiltration in organic solvent (THF or MeCN are preferred). During diafiltration excess building block $2^1$ and other chain extension reagents permeate through the membrane but, due to a combination of its high molecular weight/steric bulk/molecular architecture, the rejection of supported sequence defined polymer with one side-chain (3) is very high. The residual unreacted building block $2^1$ in the permeate may be re-purified from other reaction debris (for instance, by chromatography) and used in later coupling cycles, increasing synthetic efficiency. However, building block $2^1$ is the largest species that must permeate through the membrane (i.e. it has the highest rejection in the crude reaction mixture except for 3), and so is the one most likely to contaminate 3 after chain extension. At this stage complete purification (requiring the permeation of large volumes of solvent) is unnecessary. Instead, only enough solvent need permeate to recover the majority of building block $2^1$ (if required), and to remove any other reagents that could later react with the free hydroxyl of 4.

Once chain terminal protected sequence defined polymer 3 has been purified by diafiltration, a mild acid [e.g. dichloroacetic acid (DCA), or a low concentration of HCl] is added to this solution to effect unblocking of the acid-labile temporary protecting group (PG, FIG. 1), including a cation trapping agent (e.g. pyrrole, water, a thiol etc.) to drive the reaction to completion, if required. A second round of diafiltration is used fully to purify supported sequence defined polymer 4, now bearing a chain terminal hydroxyl ready for another round of chain extension. This process removes the acid reagent, protecting group debris and additional reagents. Critically, it also removes any last traces of building block $2^1$ that could otherwise participate in the next round of chain extension; after unblocking PG, any residual building block $2^1$ will also have been unblocked (to 5, reducing its size), and will therefore have a significantly lower rejection, making complete purification more efficient.

The retentate from diafiltration of the unblocked, supported sequence defined polymer 4 is next concentrated (by diafiltration, or by evaporation) ready for another round of chain extension (FIG. 1); concentration (particularly from THF or MeCN) conveniently removes traces of water that may have accumulated during the preceding processes, and which would consume expensive building block 2. In the same series of processes as described above, supported sequence defined polymer 4 is first reacted with the second building block ($2^2$) in the sequence; the resultant chain extended, sequence defined polymer is again purified by diafiltration to recover excess building block $2^2$; then the temporary protecting group PG is unblocked with mild acid; and finally the chain extended, hydroxyl terminated sequence defined polymer is completely purified ready for another round of chain extension. This cycle is repeated until the desired sequence is achieved.

Figure 2:
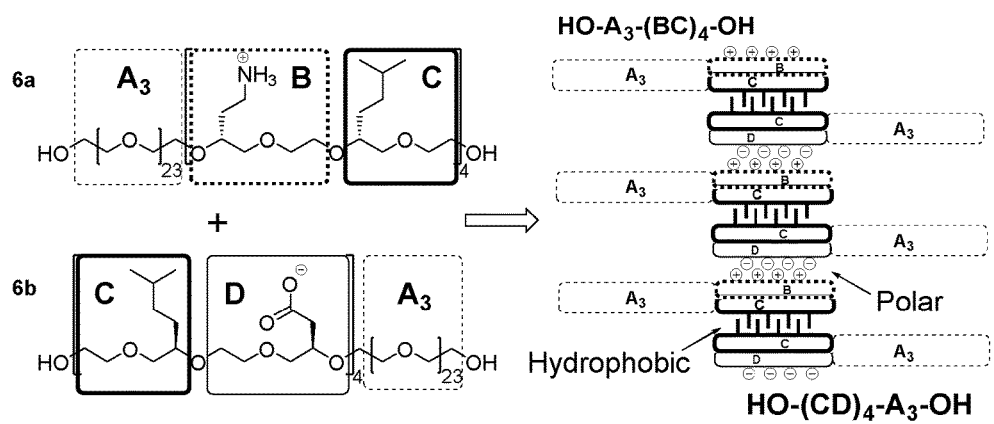
FIG. 2 illustrates how two defined monomer sequence polymers can interact in solution based on the order of their constituent monomers and the interactions of their side chains.

Once the desired sequence has been prepared, it must next be cleaved from the synthesis support and any permanent protecting groups on the side chains removed. Two target sequences of sequence defined polymers (6a and 6b) are illustrated in FIG. 2. Both may be cleaved from the synthesis support by catalytic hydrogenolysis over highly reactive palladised charcoal prepared in situ. During this procedure the azide functional group of building block B, incorporated into sequence 6a, will also be reduced concurrently to the desired amine group of the target. By contrast the bicyclic orthoester protecting group of building block D in sequence 6b will remain intact during synthesis support cleavage. Instead it will need to be unblocked separately in an additional step with stronger aqueous acid.

PEGs are well known to adopt a helical conformation in solution and in crystal structures, with four or five ethylene glycol monomer units per turn. The chirality of building blocks 2 force these helices to adopt a single handedness, with side-chains radiating radially, which should improve packing of neighbouring helices in supramolecular structures. Sequences 6a and 6b are both co-polymers consisting of a hydrophilic monodisperse PEG tail (with no side-chains) covalently bonded to an amphipathic helix. The amphipathic helix of 6a has hydrophobic isopentyl side-chains on one side, and (at neutral pH) positively charged alkyl ammonium ions on the other. The amphipathic helix of 6b also has hydrophobic isopentyl side-chains on one side, but on the other side (at neutral pH) possesses negatively charged carboxylate groups. Whilst the hydrophobic side-chains of both 6a and 6b can self-associate in aqueous solution (similarly to proteinogenic leucine zippers), larger assemblages of 6a or 6b alone will not be able to form due to repulsion of like charges. However upon mixing aqueous solutions of 6a and 6b, large scale structures will form, coated in a hydrophilic layer of molecularly uniform PEG, with a core bonded by both hydrophobic packing and ionic associations.

Many other side-chains may be prepared that confer robust intramolecular recognition, to construct precisely defined functional molecules. For instance, building blocks bearing the crown ether of side-chain D are expected to preferentially dock alkyl amines, such as side-chain B, and have been observed to thread polyamine chains. A larger pair of orthogonal recognition elements, that would be compatible with multiple rounds of Williamson ether chain extension, could be built around side-chains bearing hydrophobic adamantyl groups that insert snugly into the central void of beta-cyclodextrin.

Example 2

Preparation of a Monomeric Building Block for Use in the Preparation of a Sequence Defined Polymer Based on a PEG Backbone.

Figure 3:
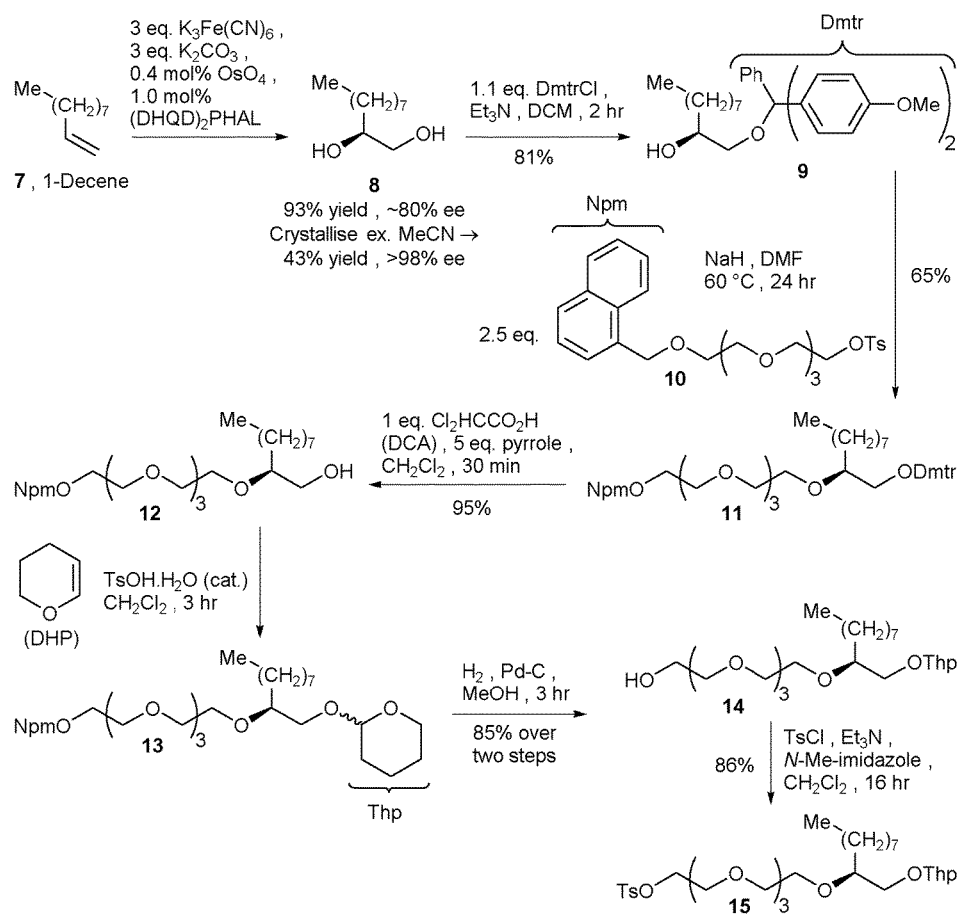
FIG. 3 illustrates the preparation of an exemplary monomeric building block used for chain extension within the scheme of FIG. 1.

FIG. 3 illustrates how a new building block bearing a side-chain may be prepared. 1-Decene (7) was subjected to asymmetric dihydroxylation using catalytic osmium tetroxide and dihydroquinidine-phthalazine [$(DHQD)_2PHAL$]. After 2 hr the reaction was quenched with sodium sulfite and the crude material extracted into ethyl acetate. Later functionalization of 4,4'-dimethoxytriphenyl (Dmtr) ether 9 as its camphanate ester demonstrated that crude decane 1,2-diol (8) had a low enantiomeric excess (ee). However, crystallisation of crude decane diol from MeCN provided 8 of high optical purity, as only one diastereoisomer of the camphanate of 9 could be detected in its $^{13}C$ NMR spectrum; typical S/N therefore suggests ee>98%. Decane diol (8) was selectively protected on the primary hydroxyl by treatment with a slight excess of DmtrCl, and Dmtr-ether 9 was etherified with excess naphthylmethyl tetragol tosylate (10) (G. Szekely, M. Schaepertoens, P. R. J. Gaffney, A. G. Livingston Chem. Eur. J., (2014), 20, 10038-10051; see Supporting Information, compound 38). The acid labile protecting group on the resultant octyl pentagol was next exchanged for a smaller one that would allow excess unconsumed building block to pass through an OSN membrane more easily (see general compound $2^1$ in FIG. 1). The Dmtr-ether of pentagol 11 was cleaved with dichloroacetic acid (DCA), forcing the reaction to completion by trapping the Dmtr$^+$ cation with pyrrole. The resultant alcohol (12) was re-protected as a tetrahydropyranyl (Thp) acetal by acid catalysed addition to dihydropyran (DHP). Intermediate 13 could not be fully purified because it co-eluted with debris from the excess DHP. Thus, crude 13 was hydrogenolysed, after which alcohol 14 could be fully purified chromatographically. The final building block 15 was prepared in good yield by sulfonation of the free hydroxyl with toluene sulfonyl chloride.

Example 3

Preparation of a Monomeric Building Block for Use in the Preparation of a Sequence Defined Polymer Based on a PEG Backbone.

Figure 4:
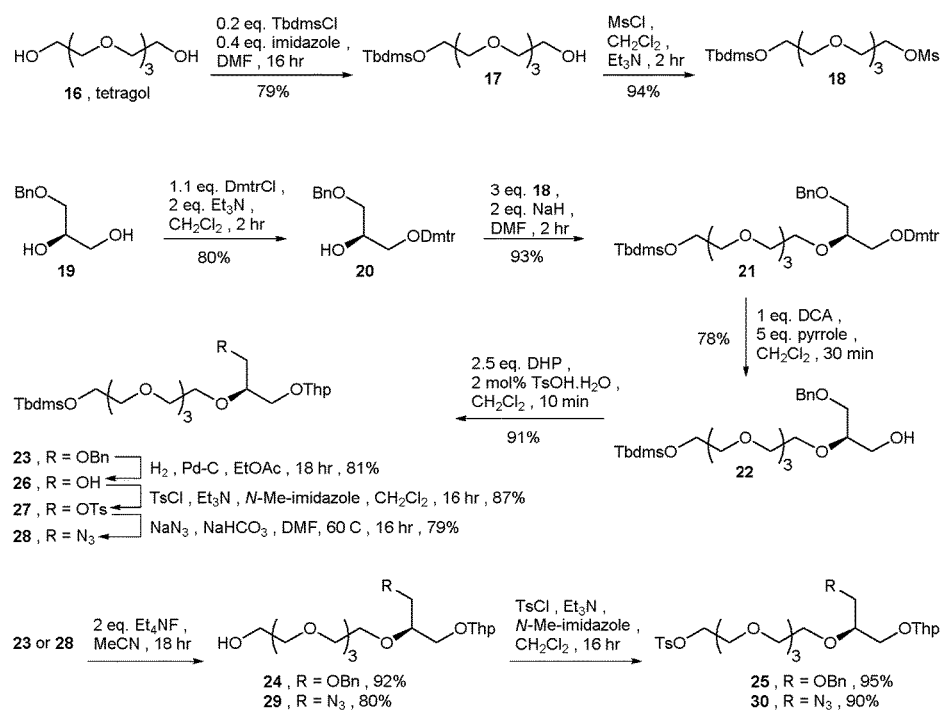
FIG. 4 illustrates the preparation of an exemplary monomeric building block used for chain extension within the scheme of FIG. 1.

FIG. 4 illustrates how new building blocks bearing functional side-chains may be prepared. Excess tetragol (16) was first desymmetrised by silylation, after which remaining unreacted tetragol was removed by partition into water, and the trace of bis-Tbdms tetragol was easily separated chromatographically. The resultant mono-silyl ether (17) was then activated by sulfonation of the remaining hydroxyl with methane sulfonyl chloride. Meanwhile, the diol of (R)-(+)-benzyl glycerol was highly regio-selectively protected on the primary hydroxyl as its 1-Dmtr ether (20) leaving the secondary hydroxyl free for attachment of a PEG chain. Attempted Williamson etherification of 20 with the toluene sulfonate of 17 gave a poor yield, with many by-products mainly derived from slow alkali driven desilylation. However, reducing the size of the electrophile by using the smaller methane sulfonate greatly accelerated this reaction, restricting the time available for slow by-product accumulation, leading to a good yield of pentagol 21. Although Dmtr-ethers are chemically compatible with our overall synthesis strategy, experience has shown that this large hydrophobic protecting group contributes some rejection with most OSN membranes, limiting the ability to separate excess building block from growing polymer homostar. Thus, pentagol Dmtr-ether 21 was selectively unblocked with DCA and pyrrole, and the resultant hydroxyl of intermediate 22 re-protected as its smaller Thp-acetal. The resultant Thp-acetal of pentagol (23), having a masked hydroxyl bearing side-chain, may be carried directly through to a finished building block (25) by initial desilylation with 1M tetraethyl ammonium fluoride in MeCN, followed by sulfonation of the intermediate alcohol (24) with TsCl. However, the benzyl ether of 23 may also be selectively unblocked allowing functional group interconversion of the exposed hydroxyl to other side-chains. Hydrogenolysis of benzyl ether 23 in methanol led to substantial simultaneous unblocking of the Tbdms-ether, presumably due to residual acidity of the Pd-catalyst. But slower hydrogenolysis of 23 in ethyl acetate gave clean conversion to the side-chain hydroxyl (26). This was activated as its toluene sulfonate (27), which was then displaced with azide. The same desilylation then sulfonation procedure as with benzyloxy substituted pentagol 23 was used to transform Tbdms-ether 28 into finished azido building block 30 via hydroxy intermediate 29.

Example 4

Coupling of Monoermic Building Blocks.

Figure 5:
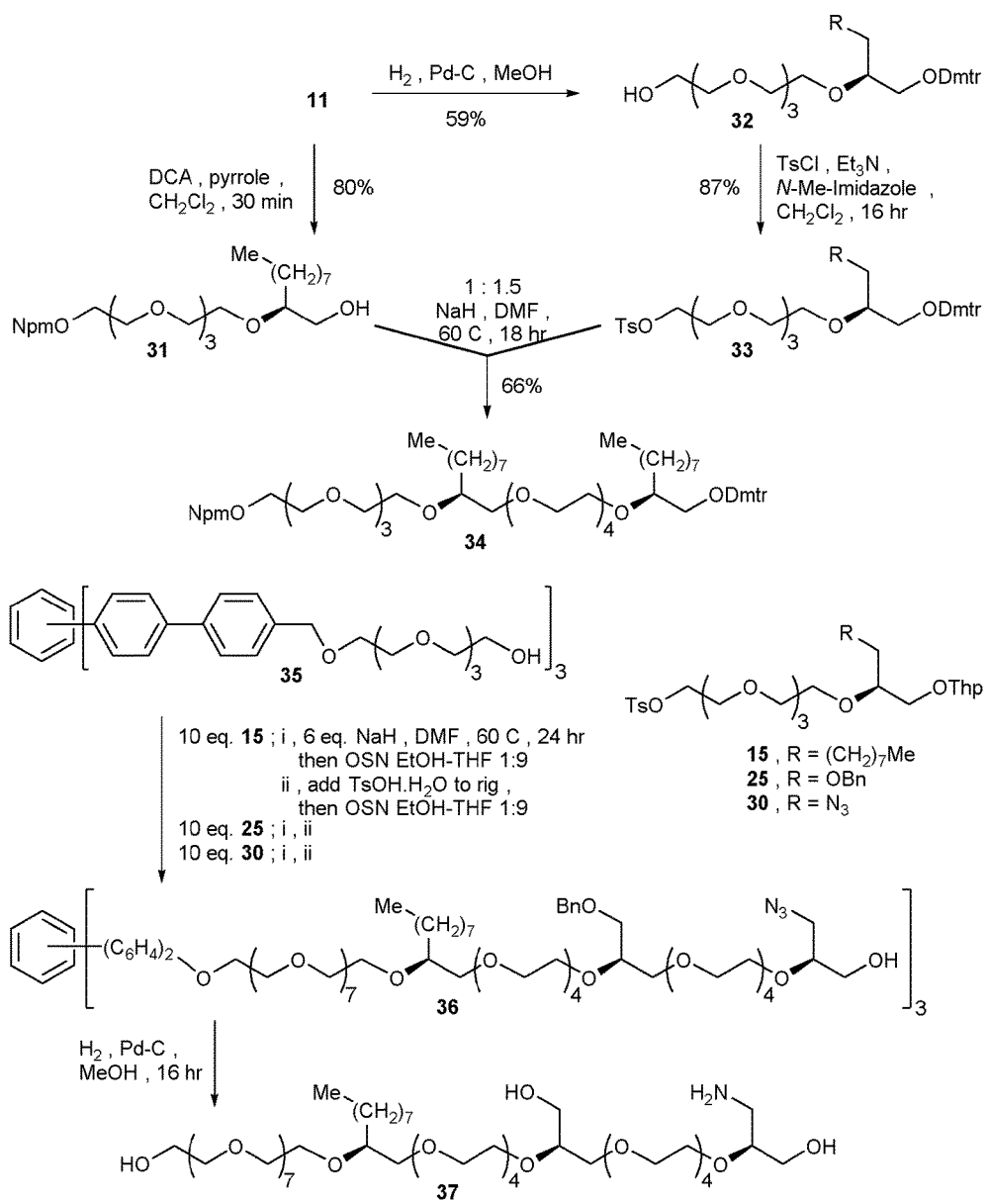
FIG. 5 illustrates the coupling of monomeric building blocks depicted in FIGS. 3 and 4.

Having regard to FIG. 5, two building blocks were prepared to exemplify the coupling strategy for chain extension. Npm-Dmtr-Intermediate 11 was selectively unblocked by detritylation at one end of the pentagol chain with DCA and pyrrole, and at the other by hydrogenolysis, to give mono-ols 31 and 32 respectively; it is also noted that hydrogenolysis of 11 in an aprotic solvent should greatly reduce the level of simultaneous detritylation which was the main by-product. In preparation for coupling, intermediate 32 was sulfonated in the usual manner; note that the least hindered hydroxyl was activated to maximise the chances of successful coupling, but if necessary a methane sulfonate could also be used.

Example 5

Preparation of Defined Monomer Sequence Polymers.

In the full homostar polymer synthesis, and having regard to FIG. 5, the Npm-protected building block 31 is the growing supported chain. Therefore, mono-hydroxy octyl pentagol Nmp-ether 31 was treated with a slight excess of octyl pentagol Dmtr-ether toluene sulfonate 33. The successful etherification to give decagol 34 demonstrates that such building blocks can be combined to prepare sequence defined PEGs with side-chains, even with a low excess of electrophile. In practise, during the preparation of monodisperse PEGs, larger excesses of the toluene sulfonate component (3.3 eq.) were usually used to ensure total conversion of the chain termini.

Thus, this example demonstrates that side-chain modified monomeric building blocks may be added in sequence to tetragol homostar 35, possessing very high membrane rejection, followed by OSN purification to recover excess building block and unblocking of the intermediate tris-Thp-acetal homostars, to give homostar supported defined sequence polymer 36. Hydrogenolysis of 36 provides octadecagol 37 with octyl, hydroxymethyl and aminomethyl side-chains at precisely defined positions, as well as with defined chirality, along its length.

While specific embodiments of the invention have been described herein for the purpose of reference and illustration, various modifications will be apparent to a person skilled in the art without departing from the scope of the invention as defined by the appended claims.

The work leading to this invention has received funding from the [European Community's] Seventh Framework Programme ([FP7/2007-2013] under grant agreement no. 238291

The invention claimed is:
1. A process for the preparation of a first compound being a non-naturally-occurring defined monomer sequence polymer, the process comprising the steps of:
(i) synthesising the first compound by performing more than one sequential monomeric coupling reaction of monomer units in a first organic solvent, wherein
all of the monomer units coupled in step (i) have an identical backbone moiety,
at least two of the monomer units coupled in step (i) have a pendent side chain moiety, said pendent side chain moieties being distinct from each other, and
at least four of the monomer units coupled in step (i) are distinct from each other; and
(ii) between each coupling reaction, separating a product of the coupling reaction from at least one second compound, which is a reaction by-product of the synthesis of the product and/or an excess of a reagent used for the synthesis of the product;
wherein during step (ii) the product of the coupling reaction and the at least one second compound are dissolved in a second organic solvent and are separated by a process of diafiltration using a membrane that is stable in the organic solvent and which provides a rejection for the product which is greater than the rejection for the second compound.

2. A process for the preparation of a first compound being a defined monomer sequence polymer, the process comprising the steps of:
(i) synthesising the first compound by performing more than one sequential monomeric coupling reaction of monomer units in a first organic solvent, wherein
all of the monomer units coupled in step (i) have an identical backbone moiety,
at least two of the monomer units coupled in step (i) have a pendent side chain moiety, said pendent side chain moieties being distinct from each other, and
at least four of the monomer units coupled in step (i) are distinct from each other; and
(ii) between each coupling reaction, separating a product of the coupling reaction from at least one second compound, which is a reaction by-product of the synthesis of the product and/or an excess of a reagent used for the synthesis of the product;
wherein during step (ii) the product of the coupling reaction and the at least one second compound are dissolved in a second organic solvent and are separated by a process of diafiltration using a membrane that is stable in the organic solvent and which provides a rejection for the product which is greater than the rejection for the second compound, with the proviso that the first compound is not an oligonucleotide, peptide or peptide nucleic acid.

3. The process of claim 1, wherein all of the monomers collectively forming the first compound are non-naturally-occurring.

4. The process of claim 1, wherein during synthesis of the first compound, the product is covalently attached to a synthesis support by an initial monomer unit.

5. The process of claim 4, wherein the synthesis support is a branch point molecule having two or more reactive moieties capable of covalently binding to the initial monomer unit.

6. The process of claim 1, wherein the first compound has a backbone selected from poly(ethylene glycol) (PEG), poly(propylene glycol) (PPG), poly(butylene glycol), poly(ethylene oxide), poly(propylene oxide), poly(butylene oxide), poly(dimethylsiloxane) (PDMS), polybutadiene, polysioprene, polystyrene, nylons and polyesters, poly(ethylene imines) (PEI), poly(propylene imines), poly(L-Lysine) (PLL), poly(amidoamines) (PAA), poly(methyl methacrylate) (PMMA), poly(vinyl benzoic acid), poly(hydroxystyrene), N-substituted glycines, and poly(lactide-co-glycolide) (PLGA).

7. The process of claim 1, wherein the first compound has a poly(ethylene glycol) backbone.

8. The process of claim 7, wherein at least one of the monomer units coupled in step (i) has chirality.

9. The process of claim 7, wherein at least one of the monomer units coupled in step (i) comprises a side chain moiety bound to a chiral carbon atom present within the backbone moiety.

10. The process of claim 7, wherein at least two of the monomer units coupled in step (i) comprise side chain moieties, each of the side chain moieties being bound to a chiral carbon atom present within the monomer unit's backbone moiety.

11. The process of claim 1, wherein the more than one sequential monomeric coupling reaction each comprise the steps of:
a) reacting a starting material with an excess of an additional monomer, the additional monomer having one of its reactive terminal protected by a protecting group, and
b) removing the protecting group so as to expose the reactive terminal such that it is ready for reaction with a subsequent additional monomer,
wherein the starting material is either an initial monomer having at least one of its reactive terminals protected, or the polymeric product of the one or more sequential monomeric coupling reactions.

12. The process of claim 11, wherein the step (ii) is performed after step a) and after step b).

13. The process of claim 1, wherein at least one or the monomer units coupled during step (i) comprises a side chain moiety comprising an active ingredient.

14. The process of claim 1, wherein the membrane is an organic solvent resistant diafiltration membrane.

15. The process of claim 13, wherein the active ingredient is a pharmaceutically active ingredient.

* * * * *